United States Patent [19]
Sano et al.

[11] Patent Number: 4,915,111
[45] Date of Patent: Apr. 10, 1990

[54] BLOOD FLOW IMAGING METHOD

[75] Inventors: Koichi Sano, Sagimihara; Tetsuo Yokoyama, Tokyo; Ryuzaburo Takeda, Mito, all of Japan

[73] Assignee: Hitachi, Ltd., Tokyo, Japan

[21] Appl. No.: 170,342

[22] Filed: Mar. 18, 1988

[30] Foreign Application Priority Data

Mar. 20, 1987 [JP] Japan ................................. 62-63763

[51] Int. Cl.$^4$ ............................................. A61B 5/05
[52] U.S. Cl. .............................. 128/653 AF; 324/306; 324/309
[58] Field of Search ................. 128/653; 324/306, 309

[56] References Cited
U.S. PATENT DOCUMENTS

| | | | |
|---|---|---|---|
| 4,532,473 | 7/1985 | Wehrli | 128/653 |
| 4,752,734 | 6/1988 | Wedeen | 324/306 |
| 4,777,957 | 10/1988 | Wehrli et al. | 128/653 |

OTHER PUBLICATIONS

Meuli et al., "MR Gated Subtraction Angiography", Radiology, vol. 159, No. 2, 5/1986, pp. 411–418.

*Primary Examiner*—Ruth S. Smith
*Attorney, Agent, or Firm*—Antonelli, Terry & Wands

[57] ABSTRACT

A sequence for detecting variations in the blood flow speed in the blood vessel is added before a measurement of imaging signals so as to determine the highest and/or the lowest speed points of time and an examined body is imaged two times at those timings. In this way the timing for setting the delay time measured from the R wave can be determined automatically and thus it is possible to obtain a blood vessel image of high quality in a short time with the minimum number of two images.

7 Claims, 5 Drawing Sheets

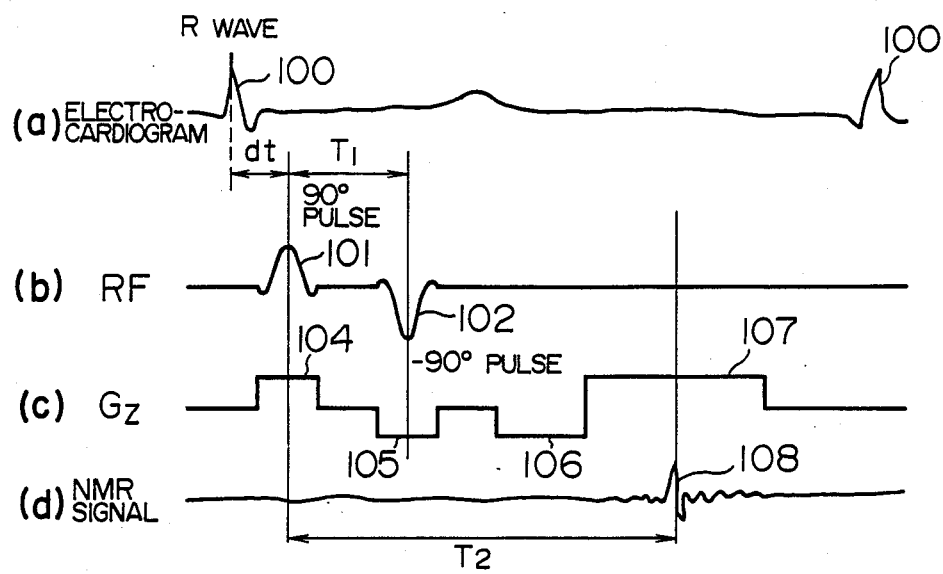
FIG. IA
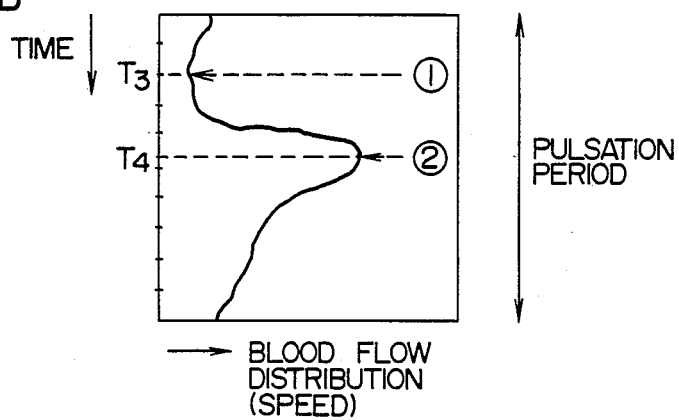
FIG. IB
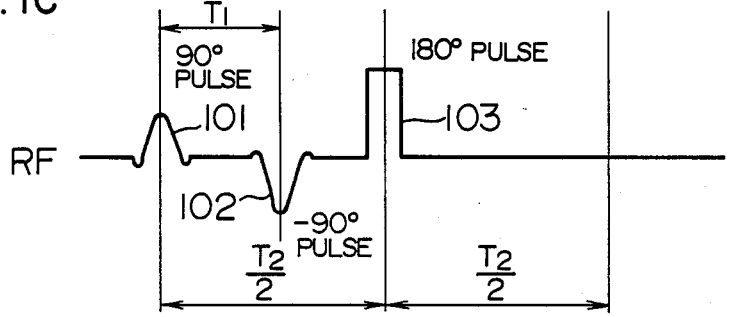
FIG. IC

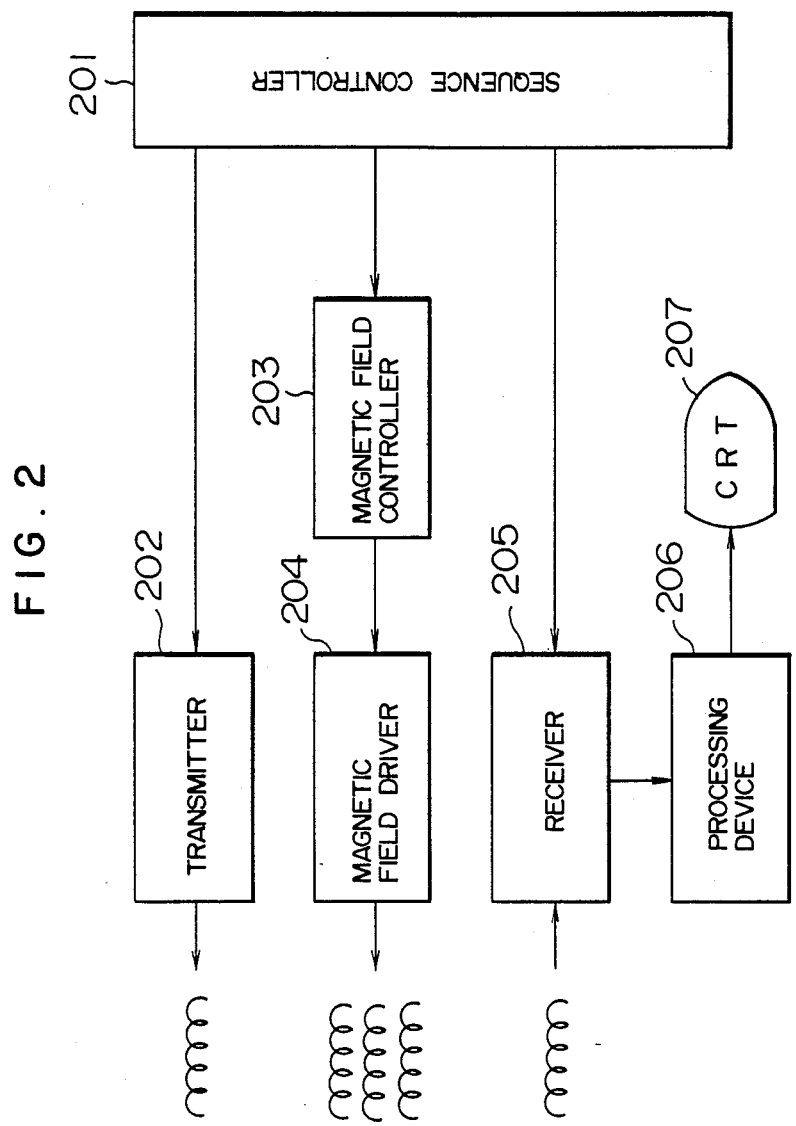

BLOOD FLOW IMAGING METHOD

BACKGROUND OF THE INVENTION

This invention relates to a tomographic method for a body, utilizing nuclear magnetic resonance phenomena, and in particular to a method for imaging blood flow in a blood vessel of a body.

A prior art representative method for imaging blood flow is discussed in JP-A-61-88132 (U.S. patent application Ser. No. 763096) or Radiology, May (1986) pp. 411–418. According to this method, using a sequence giving some influences on blood flow parts in the intensity without giving any influence on static parts, two images are scanned and blood vessel parts are extracted by using a differential image thereof so that the intensity varies only in the blood vessel parts. This principle utilizes the fact that the phase of the spin in the blood vessel varies proportionally to the speed of the blood movement and as the result the intensity varies. That is, at the imaging, when the intensity is measured in synchronism with signals coming from an electrocardiograph, the flow speed is different for the diastolic period and the systolic period of the heart. Consequently the static parts are imaged with a constant intensity and the parts including blood vessel are imaged with different intensities, when they are imaged according to the sequence described previously. Therefore only the blood vessel parts are extracted by forming the difference between these two images.

There is known another method, by which, as a measure for obtaining variations in the intensity for the blood vessel parts, instead of imaging them at two points of time, at which the flow speed is different, they are imaged according to two different sequences so that the gain in the phase variation due to the speed is different therefor at which the flow speed is the same, but its fundamental principle is the same in that variations in the phase of the spin depending on the speed is utilized.

According to the prior art techniques, in practical use, there is a problem to decide with what the imaging should be synchronized. Usually, as indicated in FIG. 1A, the R wave 100 in the electrocardiogram is detected and the imaging is synchronized therewith with a delay of dt so as to be in accordance with the variations in the flow speed. If the delay time from the R wave is not appropriately set, the difference between the two images is not significant and therefore it is not possible to obtain a precise blood vessel image. In order to overcome this inconvenience, heretofore, the imaging was effected several times e.g. with an interval of 50 m sec as the delay time, followed by an image selection process. Since usually an imaging time of about 4 to 8 minutes is necessary for one image, this method has a problem that it takes too much time to obtain one blood vessel image.

Alternatively there is another technique for measuring the flow speed by using an ultrasonic doppler apparatus as a different flow speed measuring apparatus. However it requires apparatuses other than MRI (Magnetic Resonance Imaging) apparatus. Therefore, there is a problem that it requires much time and that a region to be examined is restricted due to the doppler measuring apparatus.

SUMMARY OF THE INVENTION

The object of this invention is to provide an imaging method by using only an MRI apparatus without restricting a region to be examined, by which the setting of timing of the delay from the R wave is determined (or the setting of the delay time from the R wave is determined) and a blood vessel image can be obtained with the minimum number of 2 images without imaging a number of times by trial and error.

The above object can be achieved by adding a sequence for detecting variations in the flow speed in the blood vessel in the course of time before the measurement of the imaging signal, determining the maximum and/or the minimum speed, and imaging the examined body twice with the timing thereof.

An example of the sequence for detecting variations in the flow speed is indicated in FIG. 1A. Since the flow speed distribution at a relevant point of time can be obtained for every time when this sequence is carried out once, when this sequence is repeated e.g. in unit repeating interval of 30 m sec, variations in the flow speed in the course of time can be obtained for every 30 m sec unit, as indicated in FIG. 1B. In this example it can be known that the speed is smallest at a point of time indicated by ① and greatest at another point of time indicated by ② and the imaging signal is measured with this timing.

Taking the sequence indicated in FIG. 1A as an example, how the flow speed distribution at a certain point of time can be determined will be explained below.

At the same time as the application of a 90° pulse 101, a gradient magnetic field ($G_Z$) 104 is applied so as to select a slice and at the same time to excite the spin. After $T_1$ (e.g. about 10~20 m sec) a −90° pulse 102 is applied, and at the same time a gradient magnetic field ($G_Z$) 105 is applied so as to select the same slice. The spin of the static substance in the slice is 90°−90°=0° and thus finally it is in the same state as it is not excited. On the other hand, since the spin, which is moving and has flown out from the slice, is affected only by the 90° pulse and not by the −90° pulse, it is observed in the form of a signal for detecting the flow speed, which signal has a peak at the application of a gradient magnetic field ($G_Z$) 107 ($T_2$ after the application of the 90° pulse 101). $T_2$ is e.g. about 20~40 m sec and represents the timing when the area of the pulse for a gradient magnetic field 106 is equal to that for the magnetic field 107. The gradient magnetic field 106 is applied in order to give rise to a symmetric waveform of an NMR signal 108 having both sides with respect to the peak. When an observed signal 108 is Fourier-transformed, values are obtained for frequency components corresponding to the position. When this process is carried out for every time interval and results thus obtained are arranged time-sequentially, a curve as indicated in FIG. 1B is obtained. The timing where the flow speed is greatest and the timing where it is smallest can be determined by using the highest and the lowest points of the curve, respectively. Further it is also possible to reduce influences of inhomogeneity of the static magnetic field by applying a 180° pulse 103 at the center of $T_2$ and between the pulse 105 and the pulse 106 of FIG. 1A(c), as indicated in FIG. 1C, instead of FIG. 1A(b).

BRIEF DESCRIPTION OF THE DRAWINGS

FIG. 1A indicates an example of the pulse sequence for measuring the flow speed;

FIG. 1B indicates an example of the flow speed distribution obtained by the sequence indicated in FIG. 1A;

FIG. 1C shows another example of the RF signal used in the pulse sequence for measuring the flow speed;

FIG. 2 is a block diagram illustrating the construction of an embodiment of this invention;

DESCRIPTION OF THE PREFERRED EMBODIMENTS

Figure 3:
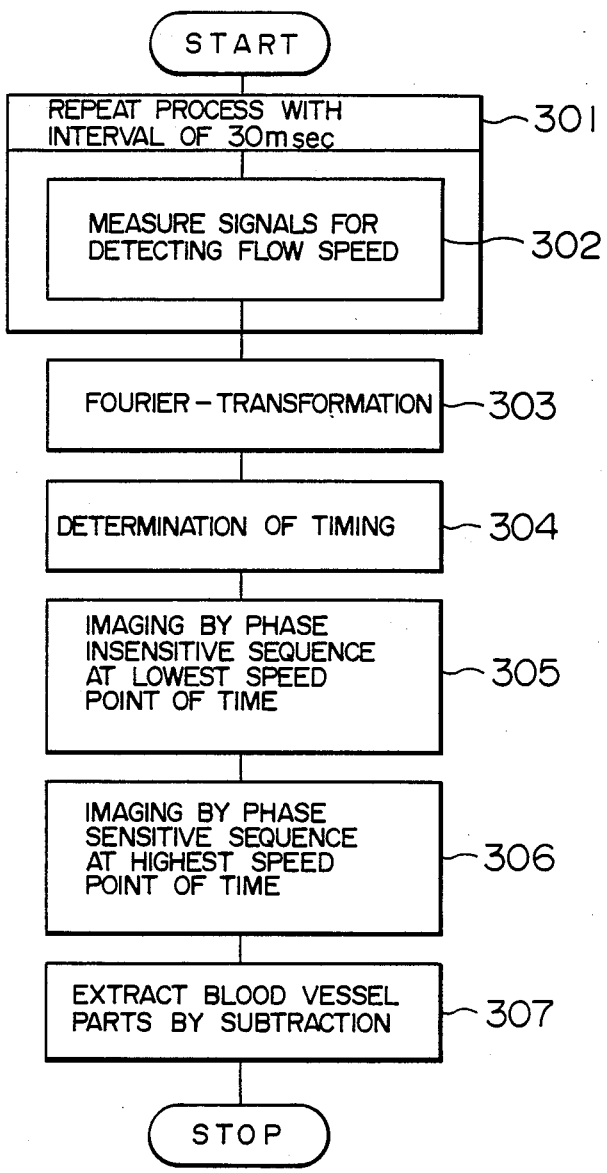
FIG. 3 is a flow chart indicating the process for realizing this invention.

Hereinbelow this invention will be explained more in detail by using some embodiments. FIG. 2 is a block diagram illustrating the construction of an embodiment of this invention. A sequence controller 201 controlling various pulses and magnetic fields generated for detecting NMR signals coming from an examined body controls a transmitter 202 transmitting high frequency pulses generated for making a specified nuclide in the examined body resonate, a magnetic field controller 203 for generating the static magnetic field determining the resonance frequency of the NMR signal and the gradient magnetic fields, whose intensity and direction can be controlled arbitrarily, and a receiver 205 effecting the measurement after having detected the NMR signal generated by the examined body. Further it carries out the reconstruction of images and various sorts of operations by means of a processing device 206, based on measurement signals taken-in from the receiver 205 and displays the images on a CRT display 207. A magnetic field driver 204 generates the magnetic fields necessary for the measurement on the basis of control signals outputted by the magnetic field controller 203 described above.

The process for realizing this invention by means of the construction stated above will be explained below, referring to FIGS. 1A to 5. The Z-direction represents the direction of the blood flow. FIG. 1A indicates an example of the pulse sequence for detecting the flow speed according to this invention and FIGS. 4 and 5 indicate two different examples of the imaging pulse sequence. FIG. 3 is a flow chart for explaining the process by means of the processing device 206. Explanation will be made below, referring to FIG. 3.

Step 301: The pulses in the sequence indicated in FIG. 1A are repeatedly applied with an interval of 30 m sec between two successive R waves 100 coming from the examined body and signals are measured for every 30 m sec.

Step 302: In the sequence indicated in FIG. 1A at first a 90° pulse 101 is applied at the same time as a gradient magnetic field ($G_Z$) 104 so as to incline the spin in a slice by 90°. Then a −90° pulse 102 is applied at the same time as a gradient magnetic field ($-G_Z$) 105. At this time the spin, which rests immobile in the slice, returns to its original state by the process 90° − 90° = 0°, but the spin flowing out from the slice (outside a period of $T_1$) doesn't feel the −90° pulse 102 and flows in the Z-direction, resting in the excited state. This signal is observed under a gradient magnetic field 107, after a gradient magnetic field 106 was applied.

Step 303: Observed signals are Fourier-transformed and arranged, as indicated in FIG. 1B.

Step 304: In FIG. 1B, the peak position ② and the valley position ① of the signal are determined. The determination may be effected either by obtaining min. and max. or in the case where noise is intense, by obtaining the highest and the lowest zones after having smoothed the curve, using the fact that the signal should vary smoothly.

Step 305: Since it is possible to know how much time the lowest speed point of time $T_3$ is separated from the R wave, based on the position of the valley ① indicated in FIG. 1B, imaging is effected at that time with a sequence indicated in FIG. 4, for which the phase doesn't vary with respect to stationary movement.

That is, an RF pulse 400 is applied at the time $T_3$ determined by using the graph indicated in FIG. 1B after the R wave 411 in the electrocardiogram. At the same time a gradient magnetic field ($G_x$) 402 for selecting a slice is applied. After that, a gradient magnetic field 403 is applied in order to cancel influences of the magnetic field 402. On the other hand a gradient magnetic field ($G_Z$) 406, 407 for reading-out is applied. Variations in the phase of the immobile spin produced by the magnetic field 406 and those produced by the magnetic field 407 are cancelled by each other, but when it moves, the phase of the spin varies. However these magnetic fields 406 and 407 act so as to cancel rotations of the phase due to movements produced by magnetic fields 408 and 409 applied at the measurement.

Furthermore a phase encoding magnetic field 405 is applied in order to separate the position in the y-direction. The intensity thereof is set to a value previously determined for every measurement, which is carried out thereafter. Usually it is varied 256 times.

Next an RF 180° pulse 401 and a gradient magnetic field ($G_x$) 404 for selecting a slice are applied in order to make dispersed phases of the excited spin uniform. At this time it is for the purpose of cancelling rotations of the phase due to movements produced by the magnetic fields 402 and 403 that the magnetic field 404 is inverted to negative. Finally a magnetic field ($G_Z$) 408 is applied together with a magnetic field 409 and a signal 410 is measured. The magnetic field 408 is applied in order to give rise to the measurement signal of a symmetric waveform having both sides with respect to the peak. At this time there are produced rotations of the phase due to movements produced by the magnetic fields 408 and 409. However they are cancelled by the magnetic fields 406 and 407, as explained previously.

Step 306: In the same way the highest speed point of time $T_4$ is determined, based on the peak position ② indicated in FIG 1B. Imaging is effected with a sequence, as indicated in FIG. 5, in which the phase varies according to the speed in that time.

Figure 4:
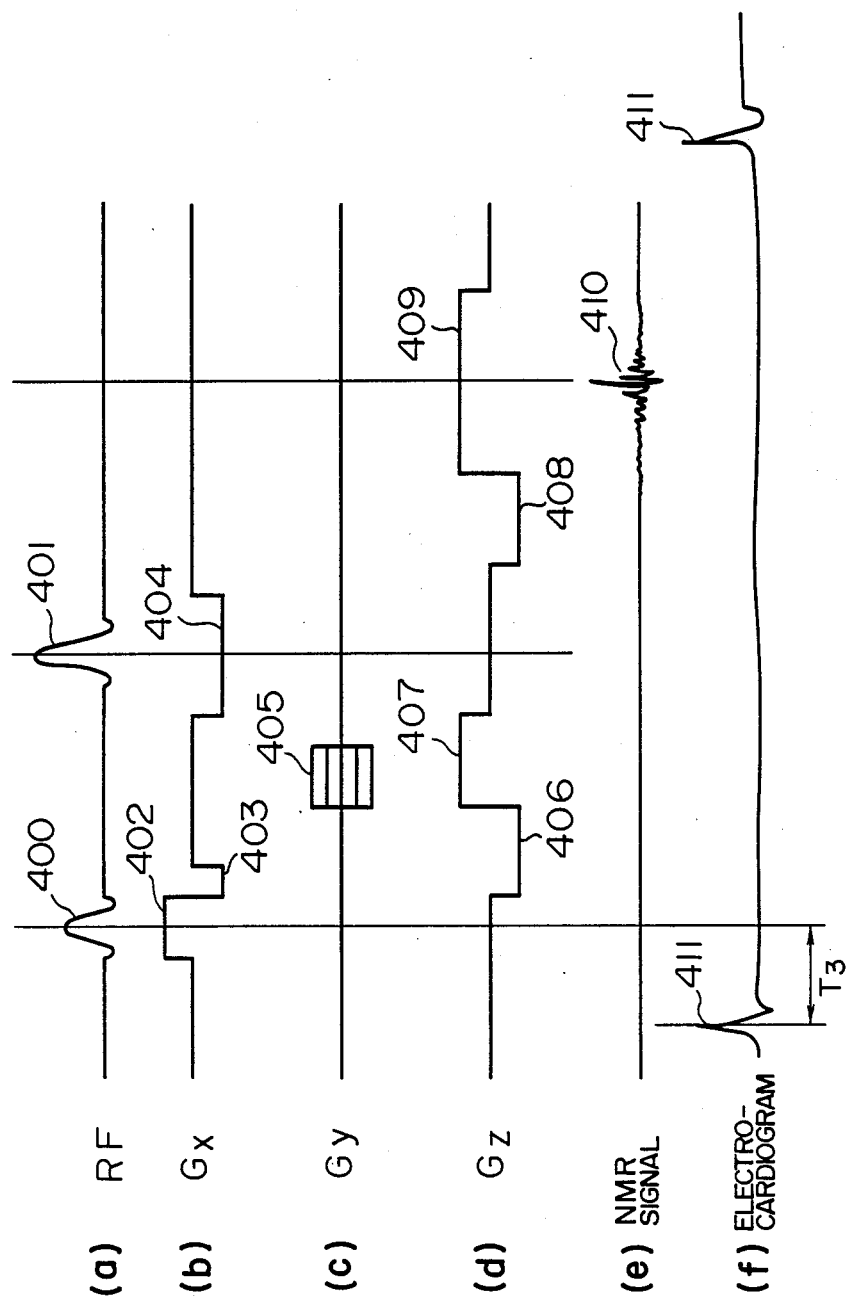
FIG. 4 indicates an example of the imaging pulse sequence suitable for measurement at the low flow speed.
Figure 5:
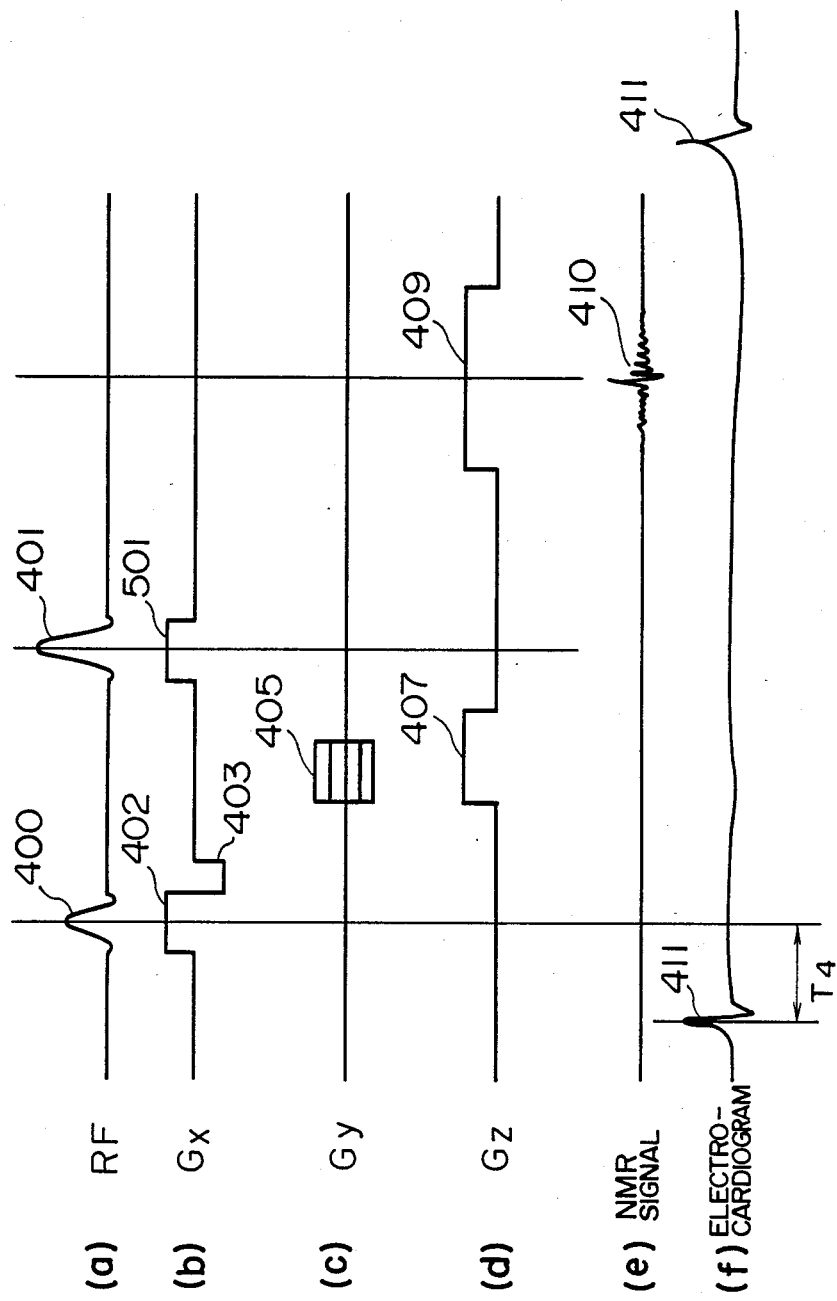
FIG. 5 indicates an example of the imaging pulse sequence suitable for measurement at the high flow speed.

Here FIG. 5 differs from FIG. 4 only in that a magnetic field 501, whose polarity is opposite to that of the magnetic field 404, is used and that the magnetic fields 406 and 408 in FIG. 4 are not here, and otherwise they are identical. This is not to produce the cancelling effect of the rotations of the phase, as understood from the explanation relating to FIG. 4 stated above. In this way it is possible to give rise to variations in the phase due to movements of the spin.

Step 307: Blood vessel parts can be extracted by forming a difference between the images obtained by Steps 305 and 306, respectively.

Further it is possible to reduce artifact due to movements of an examined body between two images by effecting alternately the signal measurements at the imaging by Steps 305 and 306 in the sequence described above and by carrying out the imaging twice at the same time. In addition the sequences in FIGS. 4 and 5 are only examples and it is a matter of course that they can be replaced by other sequences having similar functions. For example a phase insensitive sequence identical to that indicated in FIG. 4 may be applied with different timings $T_3$, $T_4$.

According to this invention it is possible to set the optimum imaging timing, because flow speed varying in the course of time in a blood vessel system can be measured in a short time without effecting any delay setting from the R wave by trial and error, and to obtain blood vessel images of high quality in a short time.

We claim:

1. A blood flow imaging method using a nuclear magnetic resonance imaging apparatus comprising means for generating a static magnetic field and gradient magnetic fields, means for generating a high frequency magnetic field, detecting means for detecting nuclear magnetic resonance signals from an examined body, and means for effecting various operations including image reconstruction, based on signals thus detected, comprising the following steps of:

repeatedly measuring speed information relating to a selected cross-sectional slice of the examined body with a pulse sequence carried out repeatedly and successively with a predetermined interval during a pulsation period, said predetermined interval being an interval sufficient for detecting a change in blood flow;

determining timings for measuring image signals and imaging pulse sequences on the basis of said repeatedly measured speed information;

carrying out the imaging pulse sequences detecting nuclear magnetic resonance signals, using said carried out imaging pulse sequences; and determining blood vessel images based on the detected nuclear magentic resonance signals.

2. A blood flow imaging method according to claim 1, wherein said pulse sequence includes a selective 90° pulse, a selective −90° pulse and a non-selective 180° pulse.

3. A blood flow imaging method according to claim 1, wherein said pulse sequence includes a selective 90° pulse, a selective −90° pulse and an inverting gradient magnetic field applied to the examined body in a direction of the blood flow.

4. A blood flow imaging method according to claim 1, wherein two different timings respectively representing a slow and a fast blood flow speed for measuring a blood flow speed are used for measuring repeatedly said image signals.

5. A blood flow imaging method according to claim 4, wherein said timings for measuring the blood flow speed are so set that the difference between two absolute speeds at said timings is maximum.

6. A blood flow imaging method according to claim 4, wherein different imaging pulse sequences are used for said different timings for measurement of image signals.

7. A blood flow imaging method according to claim 6, wherein measurement of image signals is effected with a sequence, by which signals coming from the blood vessel are the strongest, at the lowest speed measurement timing between said different timings for measurement and with a sequence, by which signals coming from the blood vessel are the weakest, at the highest speed measurement timing.

* * * * *